United States Patent [19]
Davis et al.

[11] Patent Number: 5,098,422
[45] Date of Patent: Mar. 24, 1992

[54] SANITARY NAPKIN WITH BENDABLE MEANS TO SHAPE AND RETAIN THE SANITARY NAPKIN

[75] Inventors: Martha Davis, New York, N.Y.; Daniel Formosa, Montvale, N.J.; Jeannie Gerth, Brooklyn, N.Y.; Patricia A. Moore, Montvale; Stephen Russak, Hoboken, both of N.J.; Tamara Thomsen; Tucker Viemeister, both of New York, N.Y.

[73] Assignee: McNeil-PPC, Inc., Milltown, N.J.

[21] Appl. No.: 549,335

[22] Filed: Jul. 6, 1990

[51] Int. Cl.[5] .............................................. A61F 13/15
[52] U.S. Cl. .................................. 604/385.1; 604/358
[58] Field of Search ...................... 604/385.1, 386, 387, 604/393, 395, 398, 400, 402

[56] References Cited

U.S. PATENT DOCUMENTS

4,710,187 12/1987 Boland et al. .................... 604/385.1

Primary Examiner—Randy C. Shay
Assistant Examiner—Gina Gualtieri

[57] ABSTRACT

Absorbent products for absorbing body fluids which are worn in conjunction with an undergarment are disclosed. The absorbent product comprises an absorbent core having a body facing surface, a garment facing surface and longitudinal edges. The absorbent products of the present invention utilize semi-rigid clip means for retaining the absorbent product with respect to the undergarment. Most preferably, such clip means are disposed on the garment facing surface and approximately at each lateral edge of the absorbent core. Twisting and other undesirable movement of the pad is thus reduced by a portion of the undergarment being retained between the semi-rigid clip means and the garment facing surface. Numerous alternate embodiments of clip means which grip the garment edge, as well as those which extend transversely across the garment facing surface are disclosed.

31 Claims, 6 Drawing Sheets

SANITARY NAPKIN WITH BENDABLE MEANS TO SHAPE AND RETAIN THE SANITARY NAPKIN

The present invention is directed to absorbent personal products and, more specifically, to products for absorbing body fluids worn in conjunction with an undergarment having means for retaining the absorbent product in place.

BACKGROUND OF THE INVENTION

Numerous well known absorbent products such as sanitary napkins, panty liners, incontinency pads and nursing pads are nearly always worn in conjunction with an outer garment. In other words, the absorbent product is interposed between the user's body and the outer garment.

A variety of methods of attaching absorbent products are known with the art. Early designs were simply pinned in place, while more recently one or more strips of adhesive were applied to the garment facing side of the absorbent product. The adhesive is usually placed in contact with the garment fabric and more or less anchors the absorbent product in a certain position relative to the garment.

Unfortunately, attachment to the garment using adhesive means does not present an optimal solution to the problem. As the user goes about his or her ordinary movements, the position of the garment relative to the body shifts. The absorbent product is thus subjected to the opposing forces created by a resistive force created in one direction by the adhesive and a force in the opposite direction created by the friction between the body and the absorbent product. As a result, the absorbent product may shift and may also be deformed.

For example, in the case of a sanitary napkin the longitudinal strips of adhesive applied to conventional napkins retain them in their position relative to the garment. However, the user's movements bring about a phenomenon known as "roping" whereby the edges of the napkin are laterally deformed and curled around a longitudinal axis. As a result, the napkin eventually takes on the appearance of a twisted rope. This situation causes user discomfort and a loss of product effectiveness.

The use of additional adhesive areas does not solve the above-described problems. Adhesive generally suffers from the drawback that it migrates into and is retained by the garment fabric, thus rendering the fabric "sticky", which may cause user discomfort and premature garment disposal due to adhesive build up. Moreover, a fully adhesive coated garment-facing side would not be ideal. In such a product, the garment would be forced to adhere to, and thus conform to a substantially planar surface of the absorbent product. It is known that the effectiveness of sanitary napkins and the like can be increased by causing them to take on a "channel" shape, i.e., slightly folded along a longitudinal axis. The resulting shape formed is a more effective collector of expressed fluid and has a better conformance to the user's body, thereby reducing the likelihood of leakage.

Side panels extending from the longitudinal edges of sanitary napkins, known as "flaps" or "wings" have also been used to secure napkins to the crotch portions of undergarments. However, the application and use of wings can be cumbersome. The additional adhesive may cause damage to the undergarment or the napkin itself. Moreover, this type of napkin is difficult to position on the undergarment and requires additional release paper, thus making it more costly to manufacture and less discrete to use. The wing attachment is also dependent upon the width of the undergarment — if the crotch is especially wide or narrow, the anchoring mechanism of the wings may not be as effective due to the failure of the wings to contain the undergarment.

Thus, it would be desirable to provide means for retaining the longitudinal edges of an absorbent product against the edges of a garment. It would be further desirable to provide means such that the edges of the garment were physically retained, rather than relying upon further strips of adhesive. It would also be desirable to incorporate elements into an absorbent product which would force the absorbent into a particular shapen when worn, e.g., a channel. Another desirable attribute would be the independence of the anchoring mechanism from the construction of the undergarment.

SUMMARY OF THE INVENTION

The present invention provides an absorbent product for absorbing body fluids which is worn in conjunction with an undergarment. The absorbent product comprises an absorbent core having a body facing surface, a garment facing surface and longitudinal edges. By using semi-rigid clip means for retaining the absorbent product with respect to the undergarment, the problems of unwanted movement, roping, and twisting is reduced, while the desirable channel shape is formed. In a most preferred embodiment semi-rigid clip means are disposed on the garment facing surface, approximately at each lateral edge of the absorbent core. A portion of the undergarment is thus retained between the semi-rigid clip means and the garment facing surface, creating an anchoring force which retains the absorbent product in place without undue restriction and without the use of additional adhesive.

In the most preferred embodiments a laterally extending reinforcing strap comprised of a section of material having greater rigidity than the absorbent core is attached to the garment facing surface and extends laterally between the semi-rigid clips. In the context of the products of this invention, the term "semi-rigid" is to be understood as describing a material having sufficient rigidity to retain the position of the clip against the force of the undergarments movement when the wearer is in motion. The laterally extending reinforcing strap can either be affixed to the semi-rigid clips or may be integral with them. The reinforcing strap preferably extends longitudinally along each lateral edge beyond the semi-rigid clips and preferably has at least one slit in each longitudinally extending portion in order to provide flexibility and to soften its edge against the thigh. Alternatively, a material may be chosen that can provide softness. In order to allow the product to conform to the user's body, regions of reduced bending strength are formed at the juncture of the slits. When the absorbent product is worn against the body, at least a portion of the absorbent core forms a curve about the longitudinal axis of the absorbent core. In the most preferred embodiment of the present invention the laterally extending reinforcing strap is integral with the portions extending longitudinally along the lateral edges and each longitudinally extending portion is connected to the transversely opposite portion by a portion having a substantially convex arcuate shape. Rigidity and strength are most desirable at the portion of the clip adjacent the longitudinal edge of the napkin, where the clip means contacts and retains the undergarment.

In other embodiments, as set forth below and in the Figures, the semi-rigid clip means may comprise an offset arcuate clip of a continuous section of semi-rigid material folded along a non-symmetric axis. The resulting portion having a smaller surface area is affixed to the garment facing surface of the absorbent product. Alternatively, the semi-rigid clip means may comprise a semicircular clip formed from a single flat piece of material, comprising an outer clip portion and an inner portion; the inner portion is affixed to the garment facing surface of the absorbent product. Most preferably, an offset is formed between the outer clip portion and an inner portion, whereby the portions are displaced into offset parallel planes. Also disclosed are embodiments wherein the semi-rigid clip means comprises offset arcuate clips, a first portion of an arcuate clip shaped affixed near each lateral edge of the absorbent product and a second arcuate offset portion extending inwardly toward the longitudinal centerline of the absorbent product. Most preferably, a central portion of the semi-rigid clip means has been removed to create an arcuate opening. These embodiments may also comprise a laterally extending reinforcing zone disposed on the garment facing surface and extending laterally between the semi-rigid clip means. The laterally extending reinforcing zone may be located on the undergarment-facing surface of the napkin or alternatively may be located between layers of the napkin, e.g., the absorbent and the barrier. The laterally extending reinforcing zone may also be composed of a densified cellulose board having separate clips.

In further alternate embodiments of the present invention, the semi-rigid clip means may be comprised of a base portion and at least two transversely extending flexible fingers, the base portion affixed to the garment facing surface of the absorbent product, and the flexible fingers overlying the garment facing surface of the absorbent product. In this embodiment, the material of the undergarment is interposed between the base portion and the fingers. Preferably, the fingers extend inwardly from the longitudinal edge and overlie at least 80%, or most preferably up to about 90% of the transverse width of the absorbent product. However, it may overlie as little as 5-10% of the product, so long as it clips and retains the garment.

The semi-rigid clip means may also be comprised of semicircular clip means which substantially extends to the longitudinal centerline of the absorbent product. The semicircular clip means further has snap portions extending therefrom which overlap in the vicinity of the longitudinal centerline, the snap portions are engageable to connect each of the clip means, thereby forming a structure which extends across the transverse width of the absorbent product, whereby the undergarment is disposed beneath the semicircular slip means and urged against the garment facing side of the absorbent product.

In another embodiment, the clips extend toward the longitudinal centerline of the absorbent product and an annular opening is created in one of the substantially straight portions of the clips; a post is affixed to the garment facing surface of the transverse strap, and the annular opening receives the post when the absorbent product is placed against the garment surface and the clips are placed on the opposite side of the garment, such that when compressed together the annular opening and the post retain a portion of the garment to which the absorbent product is attached.

The present invention is directed to a variety of absorbent products. For example, the use of one or more of the clips of the present invention in a sanitary napkin, panty shield, incontinence pad, diaper or nursing pad are all contemplated. The present invention is therefore not limited to the sanitary napkin described below with reference to the most preferred embodiment.

DETAILED DESCRIPTION OF THE PREFERRED EMBODIMENTS

Figure 1:
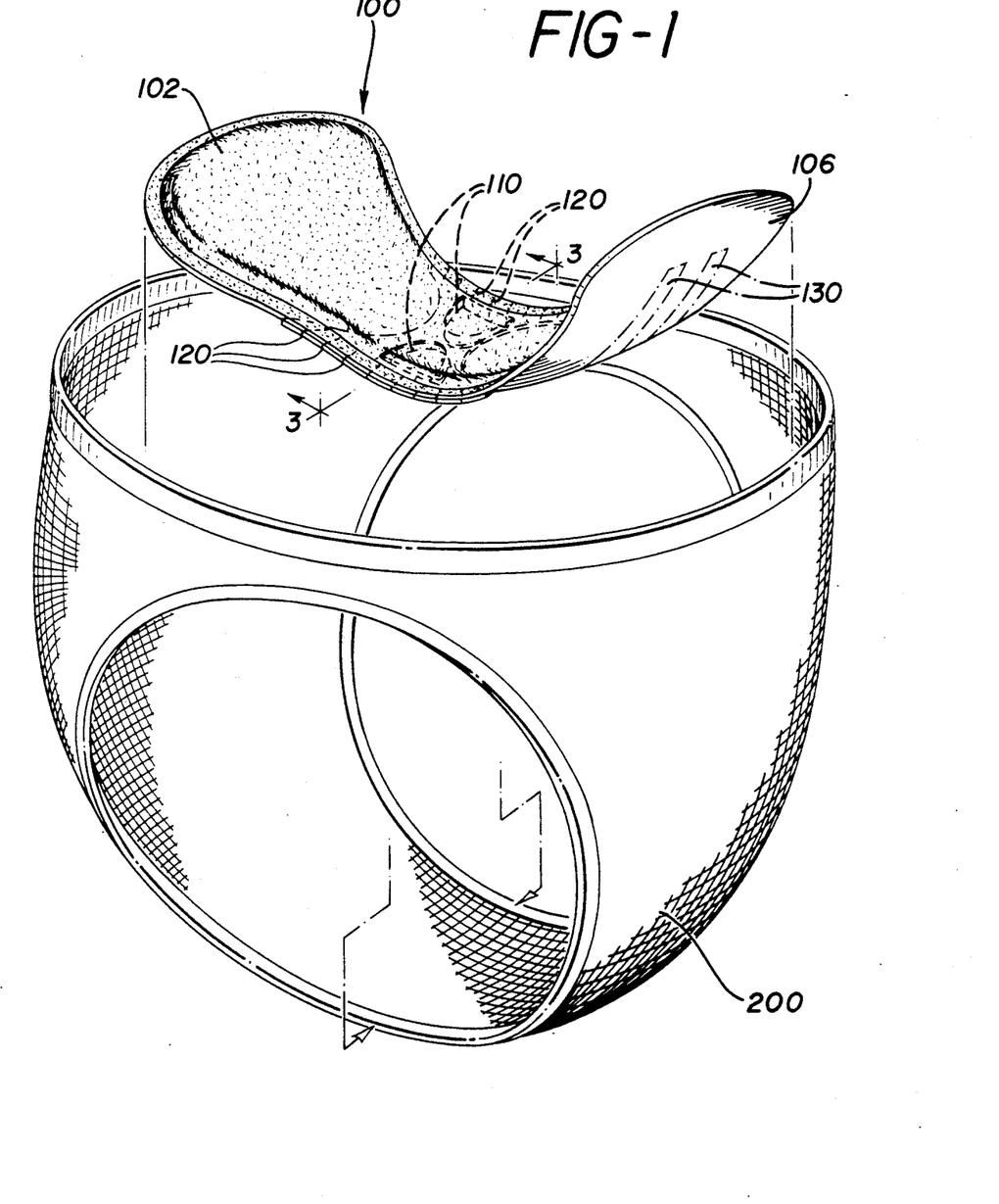
FIG. 1 provides a perspective view of a typical panty and a preferred embodiment of a sanitary napkin made in accordance with the present invention, showing the placement of the napkin within the panty.

Referring now to FIG. 1, there is depicted a typical application of the absorbent product of the present invention. As shown, a sanitary napkin 100 made in accordance with the present invention is used in conjunction with a pair of panties 200. The napkin 100 or other absorbent product is most preferably provided with at least a pair of semi-rigid clip means 110 for retaining the absorbent product 100 with respect to the undergarment. In a most preferred embodiment, the clip means 110 is affixed to the edge of the panty 200 by forcing the clip means 110 in approximately the path shown by the dashed arrows in FIG. 1.

Also visible in FIG. 1 are the slits 120 which allow the napkin 100 to conform to the user's body and the panty 200 during normal movement. In some embodiments, it will be desirable to also include conventional adhesive means 130, which generally positions the napkin 110 and further secures against its sliding out of position, particularly in the longitudinal direction. Although slitting is one means of making the napkin of this invention comfortable to use by allowing it to bend near the thighs, other means are available. For example, the edges may be scalloped fringed or scored, or the polymer of which the clip means is composed may be varied in density. Foam materials may also be placed along the edges to soften them.

Figures 2, 3:
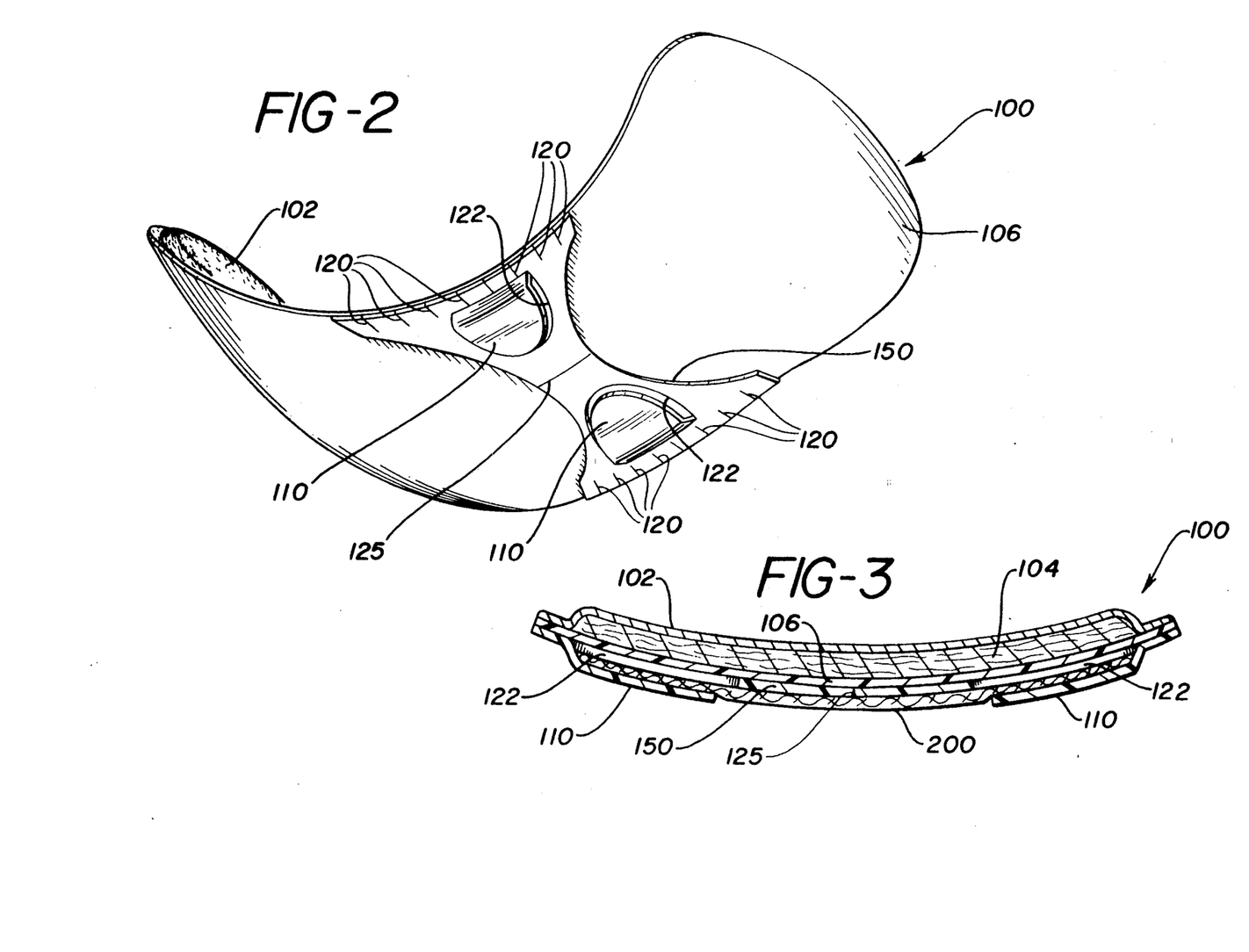
FIG. 2 is a further perspective view of the napkin depicted in FIG. 1, showing the bottom surface thereof.
FIG. 3 is a cross-sectional view of a napkin made in accordance with the present invention taken through line 3—3 in FIG. 1, and further showing the garment fabric position when the napkin is worn.

Another view of the napkin depicted in FIG. 1 is found in FIG. 2. In this view, the lateral strap 150 comprising the clip means 110 and the slits 120 is clearly visible. A line of weakness 125, such as a thinner portion, a score line, or partial slip formed in the lateral strap 150 is also visible. This element permits the napkin 100 to curve or fold along a longitudinal axis and ensures that such an axis will lie substantially along the central longitudinal portion of the napkin. It can also be seen in FIG. 2 that the clip means 110 is most preferably formed by making an arcuate cut in the lateral strap 150 and forming an offset clip 120 and leaving an underlying cutout portion 122. In order to make such a structure, it will be understood that the material of the lateral strap 150 is deformable but flexible, for example plastic, cardboard, foam, paper, reinforced nonwoven fabrics, Kevlar ®️ fabrics, Fibreglas ®️, felt, woven materials or elasticized materials. Also, the offset must be sufficient to allow the fabric of a garment such as the panty 200 depicted in FIG. 1 to be interposed and held by the friction between the clip 120 and the underlying cutout 122.

Referring now to FIG. 3, the features of the present invention discussed above are further shown. Since FIG. 3 is a cross-sectional view, the gently curved shape which the napkin most preferably takes is clearly visible. The curve of the napkin is achieved in use. Due to the flexible nature of the materials used, the napkin conforms to the shape of the panty. As explained above, this shape is preferred for absorbent articles such as sanitary napkins 100 and the like for reasons of both user comfort and absorptive efficiency. In cross-section, the layers of the absorbent structure 100 are also visible. Typically, a fluid permeable facing 102 overlies the body facing side of the absorbent structure. Beneath the facing 102 is the absorbent layer itself 104, which is followed by a fluid impermeable barrier film 106, which prevents the absorbed fluids from staining the garment to which the absorbent structure is attached. One of ordinary skill will understand that any of a number of different materials may be used for the layers described above. Moreover, numerous other absorbent constructions, comprising greater, fewer, or different types of layers are well known within the personal absorbent products art. Thus, it is understood that the present invention is not limited to the type of absorbent product with which it is used, nor is it limited to the construction of the absorbent itself.

Figure 4:
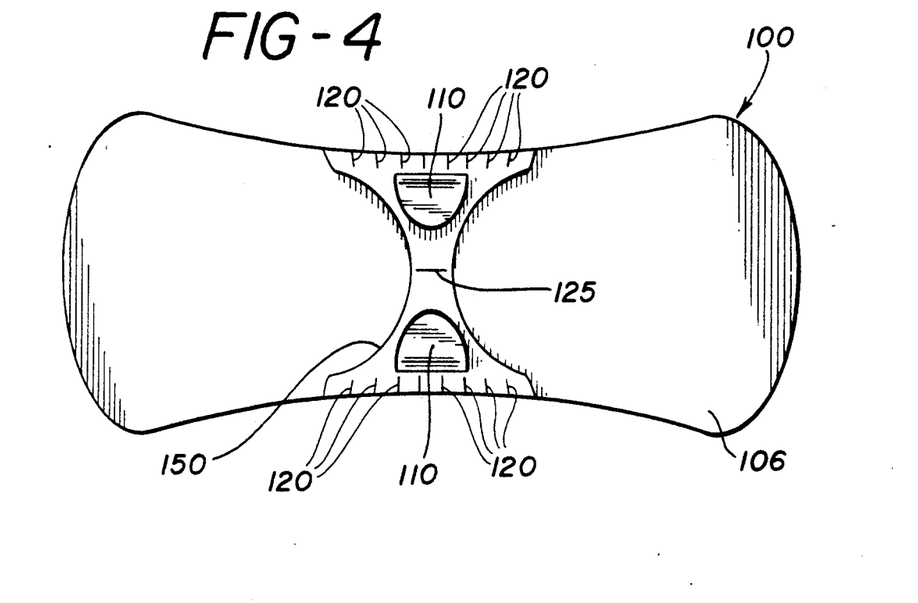
FIG. 4 is a bottom plan view of a preferred embodiment of the napkin of the present invention.
Figure 5:
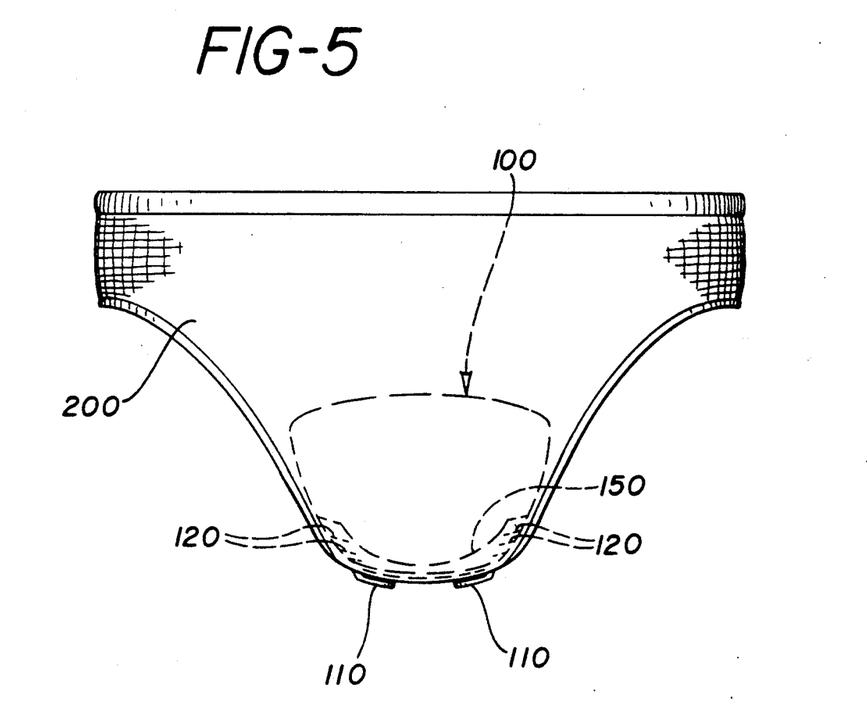
FIG. 5 is a frontal view of a panty, showing the placement of the napkin of the present invention in phantom.

The most preferred embodiment of the present invention, discussed above, is shown in a bottom plan view in FIG. 4. As shown, the shape of the absorbent product 100, the lateral strap 150, and the placement of the clips 110 and slits 120 thereon are symmetric about the longitudinal axis of the product. The line of weakness 125 is disposed along the longitudinal centerline. Thus, as shown clearly in FIG. 5, the resulting structure is one which has the capability to conform to the user's body. The clips 110 are placed over the edges of the garment 200 and, when combined with the line of weakness 125, tend to cause the absorbent to take on a flightly curved shape, as explained above with reference to FIG. 3.

Referring again to FIG. 4, the arc-shaped sides of the lateral strap 150 which forms the clip means 110 and has slits 120 formed therein are also shown. These features also contribute to the flexibility of the absorbent article 100, allowing it to comfortably conform to the perineal area of the user, or other bodily location. The slits 120 and reduction of material which results from the arc-shaped sides in the strap 150 reduce any stiffness might be caused by the material of the lateral strap 150. The shape of the strap 150 depicted also permits a smooth transition of the absorbent shape when compressed, reducing the tendency to fold or bunch in certain areas. One of ordinary skill will understand, however, that the shape of the lateral strap 150 need not be symmetric. The strap 150 can be used to force the absorbent product 100 to which it is attached into a number of configurations by manipulating the thickness of the strap 150, its shape, the length and location of the slits 130, etc.

When in place, the embodiment of the present invention depicted in FIGS. 1-5 provides a structure which conforms to the body of the user and maintains its position while the user moves about. The segmented edges formed by the slits 120 are compressed by the user's legs or other body parts or clothing. The segments most preferably have a crease, fold line or partial slit formed at their base. Thus, in use, the segments formed between the slits 120 will form the walls of a channel. The channel edges tend to act as a reinforcing rib, which transfers the compressive forces of the legs down the length of the napkin, facilitating the curved cross-section depicted in FIG. 3 along most of the length of the absorbent.

Several alternate embodiments of the present invention are depicted in FIGS. 6-12. The embodiments are all shown in bottom plan view, similar to FIG. 4. These embodiments present advantages in the simplicity of their construction, manufacture and use, which may lead to their being preferred in certain instances.

Figure 6:
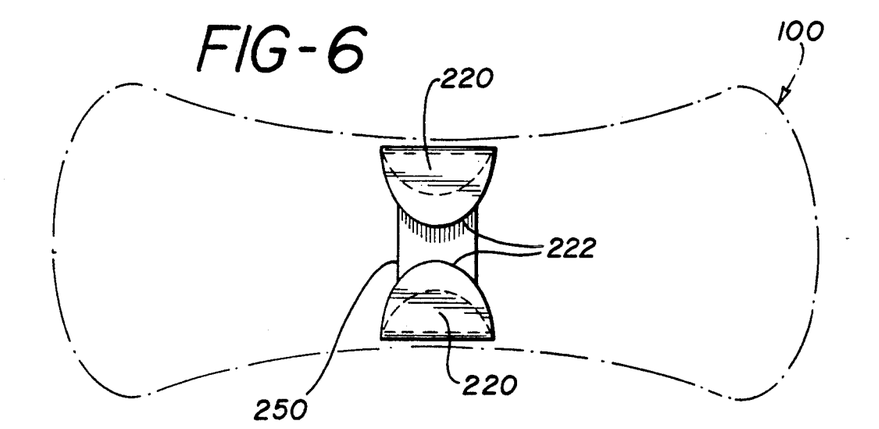
FIGS. 6–12 are bottom plan views, similar to FIG. 4, showing alternate embodiments of napkins made in accordance with the present invention.

FIG. 6 depicts an elliptical clip 220 which is folded on an off-center axis to provide tabs 222 which are of greater surface area than the portion attached to the napkin 100. The napkin Portion of the tabs 222 may be connected by a lateral reinforcing strip 250 which provides reinforcement to resist tearing or separation as the tabs 222 are pulled apart or otherwise manipulated during the application of the absorbent product 100 to the garment 200. Most preferably, the elliptical clips 220 are cut from a plastic material, which can be thermoset to create the offset tabs 222.

Figure 7:
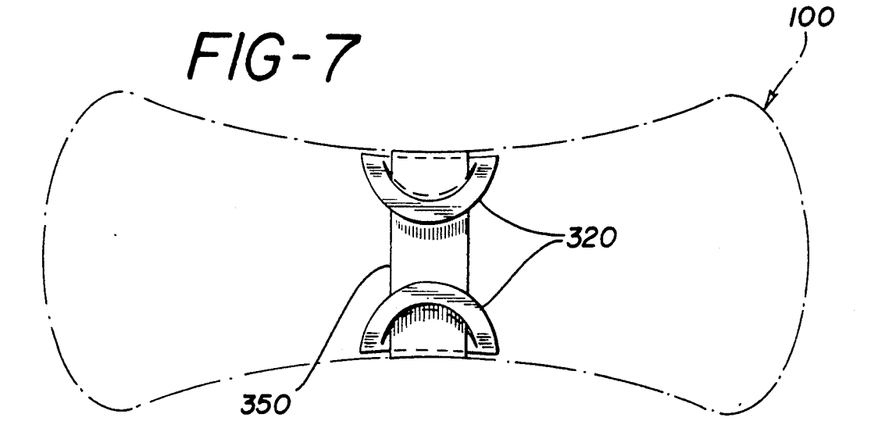

As shown in FIG. 7, the present invention can also be constructed using semicircular inwardly depending clips 320 with a transverse strap 350. Most preferably, the clips 320 are cut from a semicircle of a plastic material by cutting an arcuate slit in a flat semicircular sheet. The resulting semicircular arcuate portion is then bent with an offset sufficient to provide for the undergarment being slid between the portions of the clip 320. As shown above, a transverse strap 350 is also preferably provided.

Figure 8:
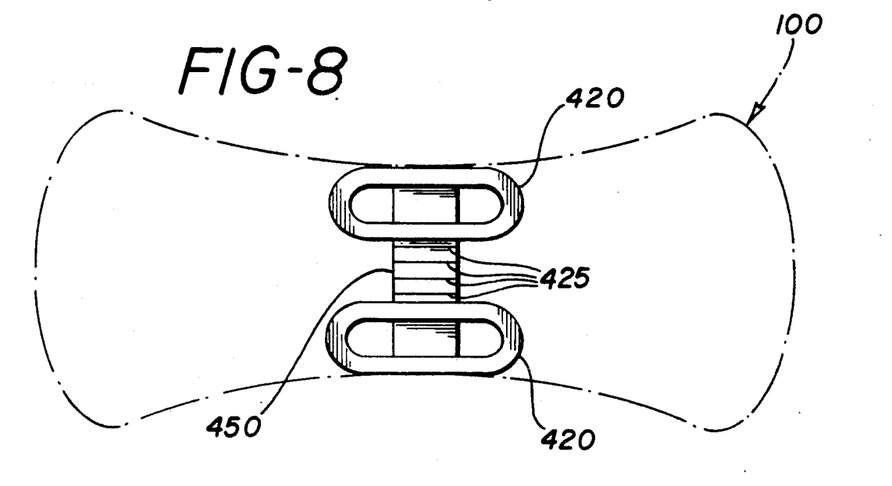

The embodiment of the present invention depicted in FIG. 8 has oval clips 420 which are most preferably individually cut from a flexible material. The clips 420 may be attached to a transverse reinforcing strap 450. The strap 450 most preferably has one or more score lines 425 or weakened areas formed along and parallel with the longitudinal axis of the absorbent article 100. The score lines 425 provide transverse hinging, allowing the absorbent article to take on a curved shape, similar to that depicted in FIG. 3 and explained above.

Figure 9:
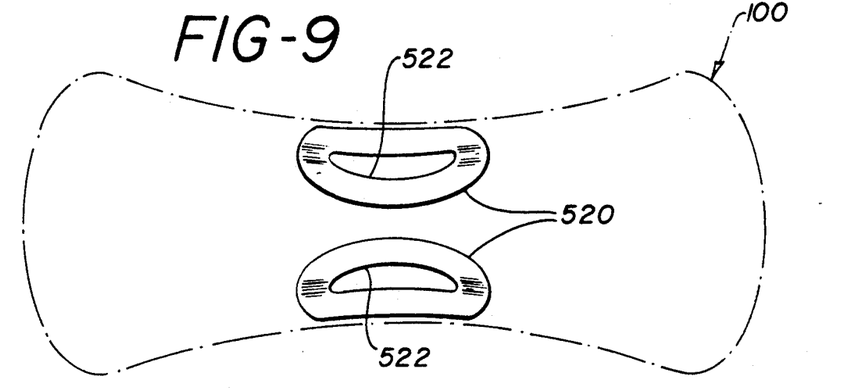

Referring now to FIG. 9, another embodiment of the present invention is depicted. In this version, arcuate inwardly depending clips 520 are provided. The clips 520 are offset, as explained with reference to other embodiments above, to permit the fabric of the garment 200 to which the absorbent product 100 is attached to be interposed between the clip 520 and the garment facing surface. The portion of the clip 520 near the longitudinal edge of the absorbent product 100 is attached directly to the garment facing surface thereof. The attachment may be produced by heat seal between the polymers of the clip and the barrier, by adhesive (e.g., hot melt adhesives, emulsions or the like) or rivets. The clip may also be sandwiched between layers of the napkin. The slot or cutout 522 provides a more flexible clip 520 and permits easier attachment of the clip to the garment.

Figure 10:
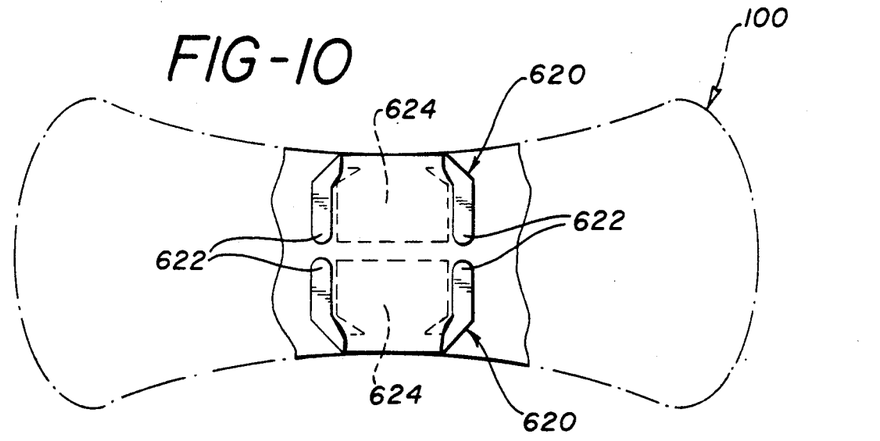

A somewhat different embodiment of the present invention is shown in FIG. 10. Two distinct plastic clips 620 are provided with inwardly directed fingers 622. Preferably the fingers 622 extend across at least between about 80% of the transverse width of the absorbent product 100, and most preferably across about 90% of the width, although it may traverse as little as 5 to 10% of the width. Unlike several of the embodiments discussed above, minimal or no offset clearance is provided between the clip bases 624 and the fingers 622. Thus, when the fabric or the garment is interposed between the bases 624 and the fingers 622 a pinching or shearing effect occurs, holding the absorbent article firmly in position.

Figure 11:
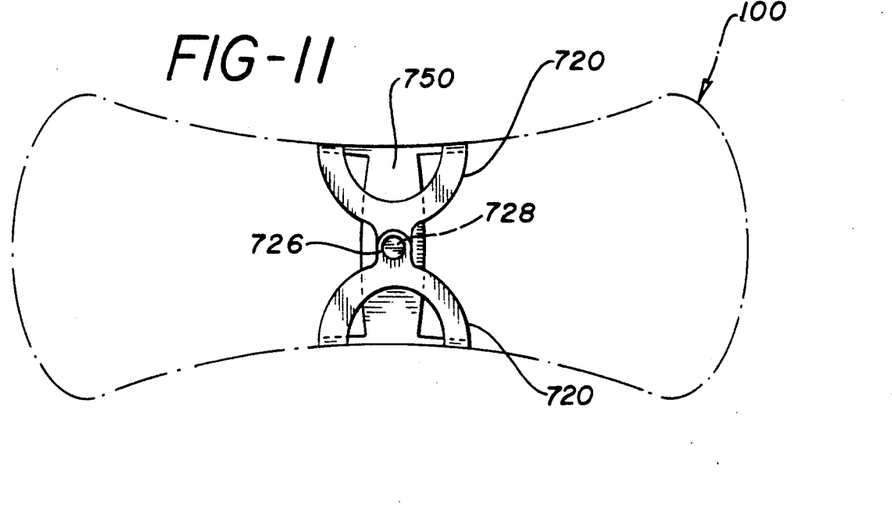

Another alternate embodiment of the present invention is depicted in FIG. 11. In this embodiment semicircular clips 720 are provided which are similar to those shown in FIG. 7, however, they are extended to almost the longitudinal centerline of the absorbent article 100. Snap portions 726, 728 extend from each of the clips 720 and overlap, most preferably in the vicinity of the longitudinal centerline. The positive connection provided by the snap portions 726, 728 help to both retain the absorbent product in place and to produce the curved shape described above with reference to FIG. 3. As will be understood by one of ordinary skill, the snap portions 726, 728 may comprise a male and female portion and either be a conventional metal snap fastener or a "post and hole" formed from or affixed to the material of the underlying clip 720. It would also be possible to utilize other types of mechanical fasteners either attached to or formed from the clip 720, e.g., tab and slot or other interlocking structures. In certain embodiments a fastening system such as VELCRO TM may also be useful. In the embodiment shown, a transverse strap 750 is also provided.

Figure 12:
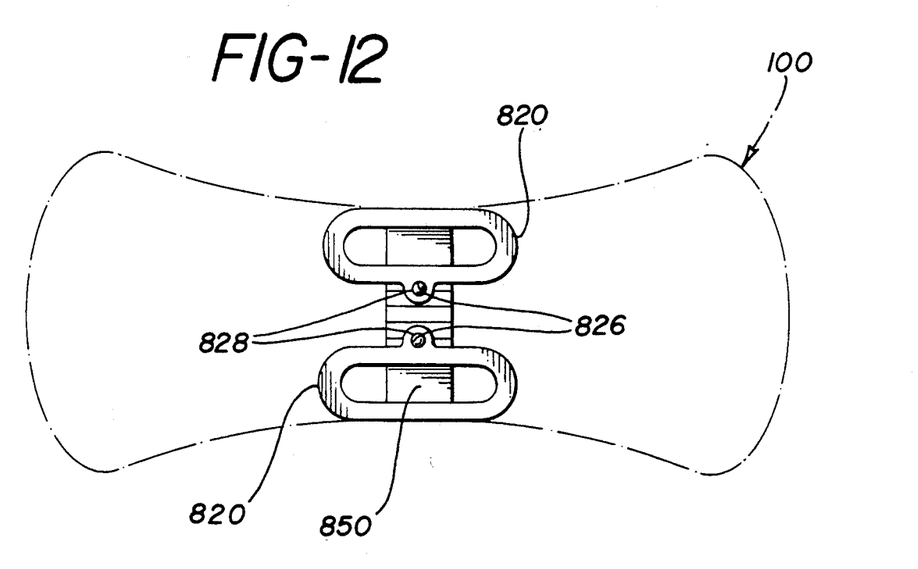

FIG. 12 depicts another alternate embodiment, similar to that of FIG. 8, however, in a manner similar to the embodiment of FIG. 11, the clips 820 are extended toward the longitudinal centerline of the absorbent product 100. As shown, an annular opening 826 is created in one of the substantially straight portions of each clip 820. The annular opening 826 receives a button or post 828 which is mounted on the garment facing side of the transverse strap 850. In this embodiment, an absorbent product is placed against the garment surface and the clips 820 placed on the opposite side of the garment 200. The post 828 is undersized relative to the annular opening so that when compressed together the annular opening and the post "pinch" a portion of the garment 200 to which the absorbent article 100 is attached.

Although certain embodiments of the present invention have been set forth with particularity, other embodiments are contemplated as being within the spirit of the invention described herein. For example, numerous variations to the fastening means described above, as well as the use of the present invention in conjunction with absorbent products other than sanitary napkins is contemplated. Accordingly, reference should be made to the appended claims in order to determine the scope of the present invention.

What is claimed is:

1. An absorbent product for absorbing body fluids which is worn in conjunction with an undergarment, the absorbent product comprising:

(a) an absorbent core having a body facing surface, a garment facing surface and longitudinal edges, said absorbent core having a longitudinal centerline; and (b) semi-rigid clip means for retaining the absorbent product with respect to an undergarment, the semi-rigid clip means being disposed on the garment facing surface at or near each longitudinal edge of the absorbent core, whereby a portion of the undergarment can be retained between the semi-rigid means and the garment facing surface.

2. The absorbent product of claim 1, further comprising a laterally extending reinforcing strap means comprised of a section of material having greater rigidity than the absorbent core, disposed on the garment facing surface and extending laterally between the semi-rigid clip means.

3. The absorbent product of claim 2, wherein the laterally extending reinforcing strap means is affixed to the semi-rigid clip means.

4. The absorbent product of claim 2, wherein the laterally extending reinforcing strap means is integral with the semi-rigid clip means.

5. The absorbent product of claim 2, wherein the laterally extending reinforcing strap means extends along each longitudinal edge beyond the semi-rigid clip means.

6. The absorbent product of claim 5, wherein the laterally extending reinforcing strap means further comprises at least one slit in each portion extending along the longitudinal edges.

7. The absorbent product of claim 6, wherein the laterally extending reinforcing strap means is integral with the portions extending longitudinally along the lateral edges, each longitudinally extending portion being connected to a transversely opposite portion by a portion having a substantially convex arcuate shape.

8. The absorbent product of claim 6, further comprising regions of increased flexibility relative to the remainder of the reinforcing strap means formed at the juncture of the slit, whereby when the absorbent product is worn against the body, at least a portion of the absorbent core forms a curve about the longitudinal axis of the absorbent core.

9. The absorbent product of claim 8, further comprising at least one further region of reduce bending strength formed in the laterally extending reinforcing strap means, the region being substantially along the longitudinal centerline of the absorbent core.

10. The absorbent product of claim 1, wherein the semi-rigid clip means comprises an offset arcuate clip said arcuate clip being offset from the plane of the garment facing surface of the product, comprised of a continuous section of semi-rigid material folded along a non-symmetric axis thereby defining a larger surface area portion and a smaller surface area portion, whereby the portion of smaller surface area is not offset from the plane of the garment facing surface of the product and is affixed to the garment facing surface of the absorbent product.

11. The absorbent product of claim 10, further comprising a laterally extending reinforcing strap means comprised of a section of material having greater rigidity than the absorbent core, disposed on the garment facing surface in substantially the same location as and extending laterally between the semi-rigid clip means.

12. The absorbent product of claim 1, wherein the semi-rigid clip means comprises a semicircular clip formed from a single piece of material, comprising an outer clip portion and an inner portion, the inner portion affixed to the garment facing surface of the absorbent product.

13. The absorbent product of claim 12 wherein the offset is formed between the outer clip portion and an inner portion, whereby the outer and inner portions are displaced into offset parallel planes.

14. The absorbent product of claim 12, further comprising a laterally extending reinforcing strap means comprised of a section of material having greater rigidity than the absorbent core, disposed on the garment facing surface in substantially the same location as and extending laterally between the semi-rigid clip means.

15. The absorbent product of claim 1, wherein the semi-rigid clip means comprises oval clip portions, a longitudinal edge of one of the oval clip portions affixed to each of the lateral edges of the absorbent product.

16. The absorbent product of claim 15, further comprising a laterally extending reinforcing strap means comprised of a section of material having greater rigidity than the absorbent core, disposed on the garment facing surface in substantially the same location as and extending laterally between the semi-rigid clip means.

17. The absorbent product of claim 16, wherein the clips extend toward the longitudinal centerline of the absorbent product and an annular opening is created in one of the clips; and a post affixed to the garment facing surface of the transverse strap, whereby the annular opening receives the post when the absorbent product is placed against the garment surface and the clips are placed on the opposite side of the garment, such that when compressed together the annular opening and the post retain a portion of the garment to which the absorbent product is attached.

18. The absorbent product of claim 1, wherein the semi-rigid clip means comprises offset arcuate clips, said arcuate clips being offset from the plane of the garment facing surface of the product a first portion of an arcuate clip shape affixed near each lateral edge of the absorbent product and a second arcuate offset portion extending inwardly toward the longitudinal centerline of the absorbent product.

19. The absorbent product of claim 18 wherein a central portion of the semi-rigid clip means has been removed to create an arcuate opening.

20. The absorbent product of claim 1, wherein the semi-rigid clip means is comprised of a base portion and at least two transversely extending flexible fingers the base portion affixed to the garment facing surface of the absorbent product, and the flexible fingers overlying the garment facing surface of the absorbent product, whereby the material of the undergarment is adapted to be interposed between the base portion and the fingers.

21. The absorbent product of claim 20, wherein the fingers extend inwardly from the longitudinal edge and overlie at least about 10% of the transverse width of the absorbent product.

22. The absorbent product of claim 20, wherein the fingers extend inwardly from the longitudinal edge and each finger overlies at least about 40% of the transverse width of the absorbent product.

23. The absorbent product of claim 1, wherein the semi-rigid clip means is comprised of semicircular clip means and further comprising snap portions extending from the semicircular clip means which overlap in the vicinity of the longitudinal centerline of the absorbent product, the snap portions being engageable to connect each of the clip means, thereby forming a structure which extends across the transverse width of the absorbent product, the undergarment being disposed beneath the semicircular clip means.

24. The absorbent product of claim 22, further comprising a laterally extending reinforcing strap means comprised of a section of material having greater rigidity than the absorbent core, adapted to be disposed on the garment facing surface and extending laterally between the semi-rigid clip means.

25. The absorbent product of claim 1, wherein the absorbent product is a sanitary napkin.

26. The absorbent product of claim 1, wherein the absorbent product is a panty shield.

27. The absorbent product of claim 1 wherein the absorbent product is an incontinence pad.

28. The absorbent product of claim 1 wherein the absorbent product is a nursing pad.

29. The absorbent product of claim 1 wherein the absorbent product is a diaper.

30. In an absorbent product for absorbing body fluids which is worn in conjunction with an undergarment, the absorbent product comprising an absorbent core having a body facing surface, a garment facing surface and longitudinal edges, the improvement comprising semi-rigid clip means for retaining the absorbent product with respect to an undergarment disposed on the garment facing surface at or near each longitudinal edge of the absorbent core, whereby a portion of the undergarment can be retained between the semi-rigid clip means and the garment facing surface.

31. A method of attaching an absorbent product for absorbing body fluids which is worn in conjunction with an undergarment to the undergarment, comprising the steps of providing an absorbent product comprising an absorbent core having a body facing surface, the garment facing surface and longitudinal edges, said absorbent core having a longitudinal centerline; and semi-rigid clip means for retaining the absorbent product with respect to an undergarment, the semi-rigid clip means being disposed on the garment facing surface at or near each longitudinal edge of the absorbent core, and placing the clip means in cooperation with an edge of the undergarment, whereby a portion of the undergarment is retained between the semi-rigid clip means and the garment facing surface.

* * * * *